US008632180B2

(12) United States Patent
Narasimha-Iyer

(10) Patent No.: US 8,632,180 B2
(45) Date of Patent: Jan. 21, 2014

(54) AUTOMATED DETECTION OF UVEITIS USING OPTICAL COHERENCE TOMOGRAPHY

(75) Inventor: Harihar Narasimha-Iyer, Livermore, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 2 days.

(21) Appl. No.: 13/449,227

(22) Filed: Apr. 17, 2012

(65) Prior Publication Data

US 2013/0100404 A1 Apr. 25, 2013

Related U.S. Application Data

(60) Provisional application No. 61/478,741, filed on Apr. 25, 2011.

(51) Int. Cl.
*A61B 3/14* (2006.01)
*A61B 3/00* (2006.01)

(52) U.S. Cl.
USPC .......................................... 351/206; 351/246

(58) Field of Classification Search
USPC ................................ 351/200–246
See application file for complete search history.

(56) References Cited

U.S. PATENT DOCUMENTS

| 2009/0244485 | A1 | 10/2009 | Walsh et al. | |
| 2012/0020539 | A1* | 1/2012 | Derr et al. | 382/131 |
| 2012/0075584 | A1* | 3/2012 | Stetson | 351/206 |

FOREIGN PATENT DOCUMENTS

WO 2010/117386 A1 10/2010

OTHER PUBLICATIONS

Michael et al., "Retinal Imaging and Image Analysis", IEEE Reviews in Biomedical Engineering, vol. 3, 2010, pp. 169-208, September.
International Search Report and Written Opinion received for PCT Patent Application No. PCT/EP2012/057416, mailed on Sep. 7, 2012, 14 pages.
Agarwal et al., "High-Speed Optical Coherence Tomography for Imaging Anterior Chamber Inflammatory Reaction in Uveitis: Clinical Correlation and Grading", American Journal of Ophthalmology, vol. 147, No. 3, Mar. 2009, pp. 413-416.
Agarwal et al., "Using OCT to Assess Anterior Chamber Inflammation", Ophthalmology Times Europe, vol. 4, No. 2, Mar. 1, 2008, pp. 1-4.
Kim, Stephen Jae., "The Role of Imaging in the Diagnosis and Management of Uveitis", Expert Review Ophthalmology, vol. 5, No. 5, Oct. 2010, pp. 699-713.
Lee et al., "In vivo Optical Frequency Domain Imaging of Human Retina and Choroid", Optics Express, vol. 14, No. 10, May 15, 2006, pp. 4403-4411.
Leitgeb et al., "Ultrahigh Resolution Fourier Domain Optical Coherence Tomography", Optics Express, vol. 12, No. 10, May 17, 2004, pp. 2156-2165.
Lowder et al., "Anterior Chamber Cell Grading with High-Speed Optical Coherence Tomography", Investigative Ophthalmology & Visual Science, vol. 45, E-Abstract 3372, 2004, pp. 1-2.
Wojtkowski et al., "Three-Dimensional Retinal Imaging with High-Speed Ultrahigh-Resolution Optical Coherence Tomography", Ophthalmology, vol. 112, No. 10, Oct. 2005, pp. 1734-1746.

\* cited by examiner

*Primary Examiner* — Mohammed Hasan
(74) *Attorney, Agent, or Firm* — Morrison & Foerster LLP

(57) ABSTRACT

Systems and methods for automatically detecting, classifying and quantifying clumps indicative of inflammation in the eye using optical coherence tomography images are described. Clump detection relies on both intensity and geometric thresholding. Applications of the invention include improved diagnosis, classification and monitoring of inflammatory disease.

27 Claims, 4 Drawing Sheets
(1 of 4 Drawing Sheet(s) Filed in Color)

(a) (b)

(a)

501

(b)

(a)

(b)

AUTOMATED DETECTION OF UVEITIS USING OPTICAL COHERENCE TOMOGRAPHY

PRIORITY

This application claims priority to U.S. Provisional Application Ser. No. 61/478,741 filed Apr. 25, 2011, hereby incorporated by reference.

TECHNICAL FIELD

The invention described herein relates to improved diagnosis in the field of ophthalmology. In particular the invention describes an automated method to detect, classify and quantify clumps indicative of inflammation in the eye using optical coherence tomography images.

BACKGROUND

Uveitis is swelling and inflammation of the uvea, the middle layer of the eye. The uvea consists collectively of the iris, the choroid, and the ciliary body. Uveitis can exist in the front of the eye (anterior uveitis or iritis), the middle region of the eye (intermediate uveitis), the back of the eye (posterior uveitis), or throughout the eye (panuveitis or diffuse uveitis). The most common form of uveitis is anterior uveitis, which involves inflammation in the front part of the eye, usually the iris. Anterior uveitis can be divided into acute and chronic types based on the duration of the inflammation. A further classification is granulomatous and non-granulomatous. Granulomatous uveitis presents with large, greasy precipitates on the corneal endothelium with large clumps of inflammatory cells present in the anterior chamber because of exuberant macrophage activity. Nongranulomatous uveitis presents with fine cornea endothelial precipitates and anterior chamber activity (clumps). Uveitis can be graded based on the number of cells present in the aqueous according to the Standardization of Uveitis Nomenclature (SUN). Slit-lamp examination is the standard method for assessment of the inflammatory reaction in case of uveitis. However clinical assessment is subjective and often difficult in eyes with corneal opacification.

Optical Coherence Tomography is a non-invasive, in-vivo imaging technique based on the back-scatter or reflectivity of light in a medium. In ophthalmic examinations, the beam of light produced by the OCT device scans the eye through the pupil and the image formation process records the back-scattering profile of the light at each location. The amount of scatter is indicative of the reflectivity of the tissue encountered, and a grayscale cross-sectional image is formed as the light beam sweeps across the field of view (FOV). OCT imaging has dramatically advanced ophthalmic diagnostic capabilities and led also to better understanding of ocular anatomy. It is an established basis of routine ophthalmic practice. Several implementations of OCT have been developed including time domain (TD-OCT) and frequency domain (FD-OCT) (spectral domain (SD-OCT) and swept-source (SS-OCT)).

The clumps of inflammatory cells present in the anterior chamber of patients with uveitis appear as bright or hyperreflective spots in OCT images. US 2009/0244485 describes a method for determining or assessing risk of uveitis based on the intensity levels of the image signal as compared to a database of normal and abnormal values. Agarwal et al compared manual and automated counting of the hyperreflective spots in OCT images of the hyperreflective spots in anterior chamber OCT (Agarwal et al "High Speed Optical Coherence Tomography for Imaging Anterior Chamber Inflammatory Reaction in Uveitis: Clinical Correlation and Grading" Am J Ophthalmology 147(3): 413-416 2009). The images were post-processed using Matlab.

The methods described above are based on a numerical count of the number of cell clumps. The present invention introduces the concept of using OCT for providing an automated measurement of the shape and volume of these clumps. A further inventive aspect is the classification of the clumps into different types such as pigment clumps and cell clumps based on the reflectivity, size, shape and other parameters. Differentiating cells and cell clumps from pigment clumps would allow the level of cells present (an indication of disease status) to be estimated independent of surgical events that might release pigment from the iris into the anterior chamber.

SUMMARY

The present invention describes a method for automatically segmenting, classifying and quantifying clumps indicative of inflammation in the eye using OCT images. The methods described herein can provide a quantitative measure of the number and density of hyper-reflective clumps in the anterior chamber. It will also be possible to classify different types of hyper-reflective spots (i.e. pigment clumps vs. cell clumps) and quantify their density separately. By automating the process of clump detection using OCT imaging and image processing, the present invention removes the subjectivity of manual slit-lamp evaluation technique for assessing the inflammatory reaction. While the invention described herein applies to uveitis, it could be applied to any inflammation of the eye involving the presence of cellular clumps in the anterior chamber of the eye.

The methods described herein can be applied to the following situations:

1. Analysis of anterior segment OCT images for Uveitis diagnosis.
2. Analysis of posterior segment OCT images for diseases that cause hyper-reflective spots to occur in the vitreous.
3. Analysis of anterior segment images to obtain quantitative measurements—hyper-reflective spot count/B-Scan, density etc.
4. Provide a way to visualize hyper-reflective spot detection to the user.
5. Monitoring of treatment efficacy, progression of disease.

BRIEF DESCRIPTION OF FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
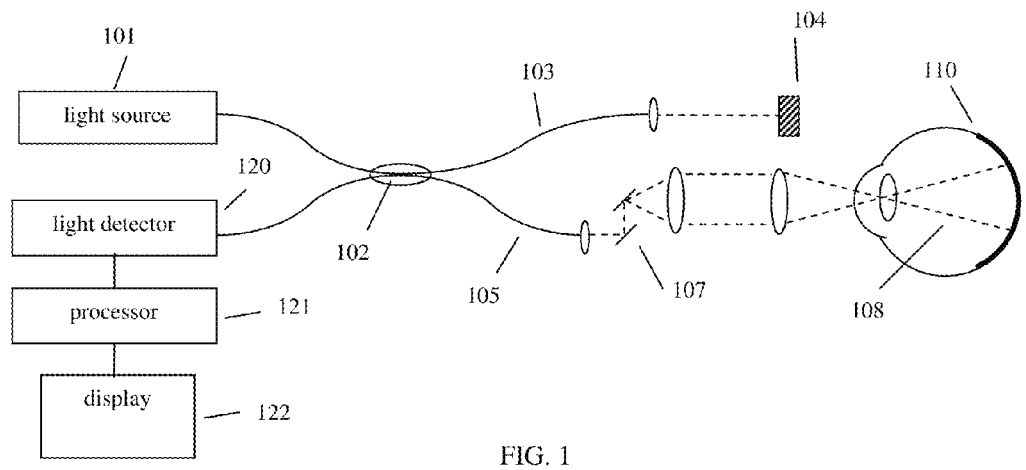
FIG. 1 is a generalized OCT instrument that can be used to provide data for the present invention.

An optical coherence tomography scanner, illustrated in FIG. 1 typically includes a light source, 101. This source can be either a broadband light source with short temporal coherence length or a swept laser source. (See for example, Wojtkowski, et al., "Three-dimensional retinal imaging with high-speed ultrahigh—resolution optical coherence tomography," *Ophthalmology* 112(10):1734 2005 or Lee et al. "In vivo optical frequency domain imaging of human retina and choroid," *Optics Express* 14(10):4403 2006)

Light from source 101 is routed, typically by optical fiber 105, to illuminate the sample 110, a typical sample being tissues in the human eye. The light is scanned, typically with a scanner 107 between the output of the fiber and the sample, so that the beam of light (dashed line 108) is scanned laterally (in x and y) over the area or volume to be imaged. Light scattered from the sample is collected, typically into the same fiber 105 used to route the light for sample illumination. Reference light derived from the same source 101 travels a separate path, in this case involving fiber 103 and retroreflector 104. Those skilled in the art recognize that a transmissive reference path can also be used. Collected sample light is combined with reference light, typically in a fiber coupler 102, to form light interference in a detector 120. The output from the detector is supplied to a processor 121. The results can be stored in the processor or displayed on display 122. The Fourier transform of the interference light reveals the profile of scattering intensities at different path lengths, and therefore scattering as a function of depth (z-direction) in the sample (see for example Leitgeb et al, "Ultrahigh resolution Fourier domain optical coherence tomography," *Optics Express* 12(10):2156 2004). The profile of scattering as a function of depth is called an axial scan (A-scan). A set of A-scans measured at neighboring locations in the sample produces a cross-sectional image (tomogram or B-scan) of the sample. A collection of B-scans makes up a data cube or cube scan.

Figure 2:
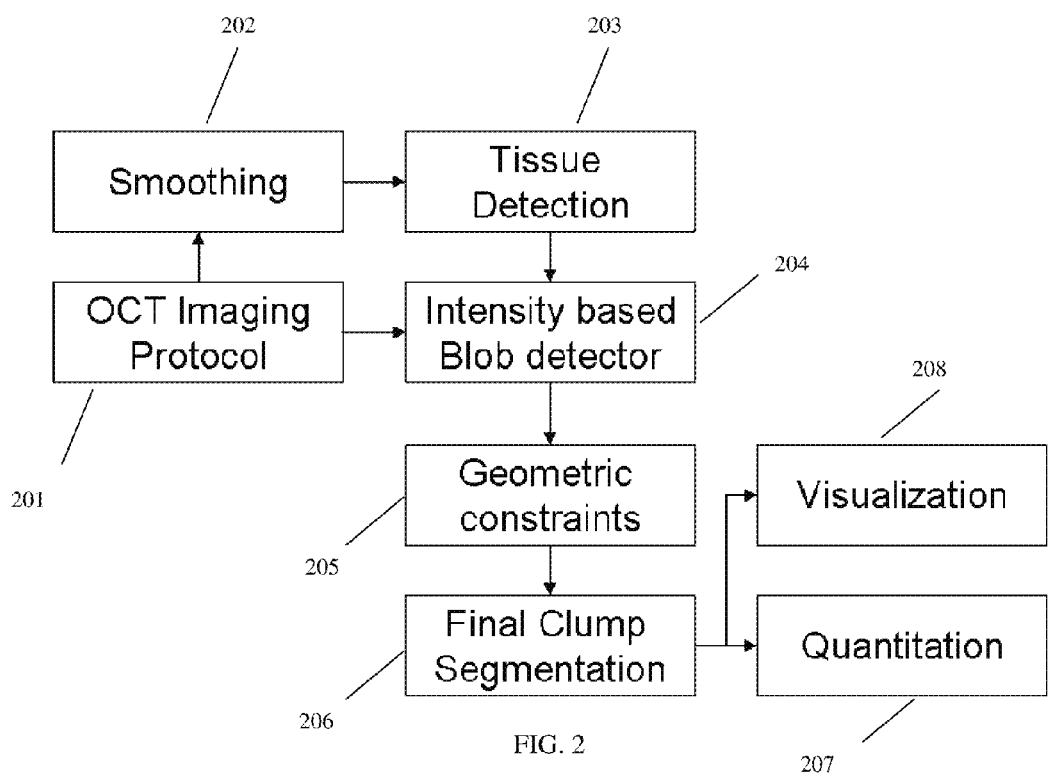
FIG. 2 is a flow chart illustrating the steps of the invention.

The different elements of the present invention are shown in FIG. 2. The method starts with OCT image acquisition 201. The method described here could be applied to different types of OCT scans. For example, it could be applied to high definition OCT B-Scans that have been speckle reduced (1024× 1024 B-Scans averaged 4 times or 20 times) or individual B-Scans from cube scans. The only requirement is that the axial and lateral resolution of the OCT image should be sufficient to visualize the cell clumps. In order to get 3D information, the B-Scans should also be spaced close enough to capture the extent of the clumps. A specific scan pattern could be 21 B-Scans, each with 1024×1024 points over a 6 mm scan region along the x dimension, 2-mm scan depth. The B-Scans could be separated by 10 microns to give a total sampling volume of 6 mm×2 mm×0.2 mm. Higher density scans could be imagined, especially with the advent of very high speed swept-source OCT systems.

Once OCT image data is obtained, the second step in the process is a smoothing of the image data to reduce noise 202. This might be accomplished using linear filters such as Gaussian smoothing filters, box filters or non-linear filters such as median filters, anisotropic diffusion filters or bilateral filters. Non-linear filters are better suited for smoothing because of their edge-preserving characteristics while suppressing noise. An optional step in the processing might be to sub-sample the image to obtain a lower resolution image. This step might be done if it is desirable to speed up the processing time and if the original image resolution was sufficiently high so that down-sampling does not affect the visualization of the structures of interest.

We are interested in segmenting the cell-clumps that appear in the anterior chamber or the posterior chamber of the eye. Hence it is desirable to detect and exclude the tissue regions in the image from further processing 203. The tissue region to be excluded corresponds to the cornea in the case of an anterior segment scan and the retina in the case of a posterior segment scan. For example, in anterior segment scans, once the cornea is detected, the clump detection can be carried out on regions below the posterior cornea. In the same way for a posterior segment scan, the clump—detection would be carried out on regions above the retina. Thus this step is mainly aimed at extracting the region of interest within the image where the clump detection would be executed. Various methods have been described in the literature previously for the segmentation of the above structures and those skilled in the art can easily adapt any existing methods for this purpose.

Figure 3:
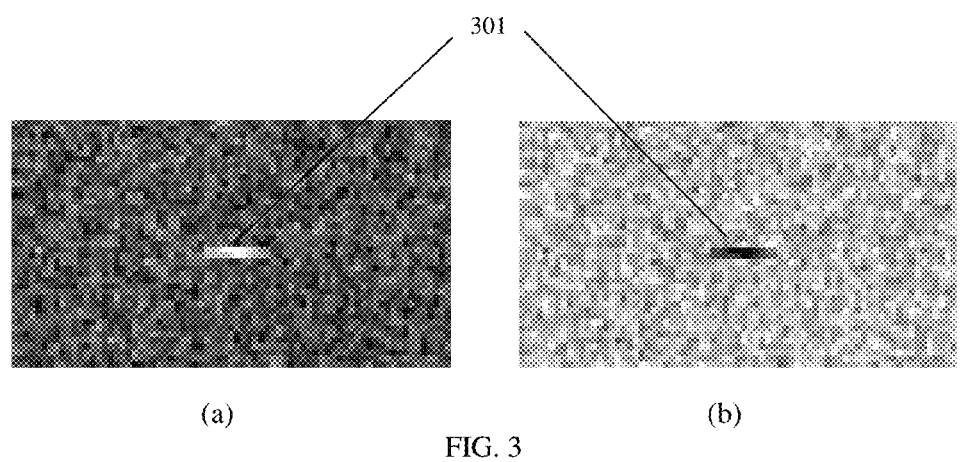
FIG. 3 shows cell clumps in (a) normal and (b) inverted grayscale images.

Once the region of interest is determined, the next step in the process is to identify the clump locations. One possible implementation of this is described here and is referred to as intensity based blob detection 204. Additional implementations can be imagined by one skilled in the art. The clumps typically appear as bright spots against the relatively low intensity vitreous humor (the clear gel that fills the space between the lens and the retina of the eyeball) or the aqueous humor (thick watery substance filling the space between the lens and the cornea). FIG. 3(a) shows the zoomed in view of a cell clump 301 obtained from the anterior chamber of the eye. FIG. 3(b) shows how the clump 301 might be visualized better using an inverted gray-scale image.

These bright intensity blobs can be segmented 204 using an adaptive thresholding strategy that adjusts itself to the local intensities in the image. Consider a pixel at location (x,y,z). The intensities of the image inside a box of size (W1×W2× W3) centered at location (x,y,z) are extracted from the image and the mean (or the median) of these intensities are calculated. The dimensions of the box—W1, W2 & W3 can be chosen based on the pixel resolutions and on the expected size of the clumps so as to enclose the full clump in a box. Now the central pixel at (x,y,z) can be marked as belonging to a clump if the intensity at (x,y,z) is significantly more than the mean intensity within the box. This strategy allows the thresholding to be much more robust to local intensity changes across the image. The above process is repeated at each of the pixel locations in the region of interest identified earlier. The result of this step is a binary mask with "ones" indicating possible clump locations and "zeros" indicating background regions. FIG. 4(a) shows a sample image that can be processed using the present invention. The image is shown in inverted gray scale to enhance visualization of clumps 401 in the aqueous humor 402 (light background area). The top layer shown in the figure is the posterior cornea 403. FIG. 4(b) shows the associated binary detection mask for a single slice based on the blob segmentation. As can be seen, this binary mask is noisy and needs to be further processed to segment only the clumps. This is done using morphological operations as will be described next.

Figure 4:
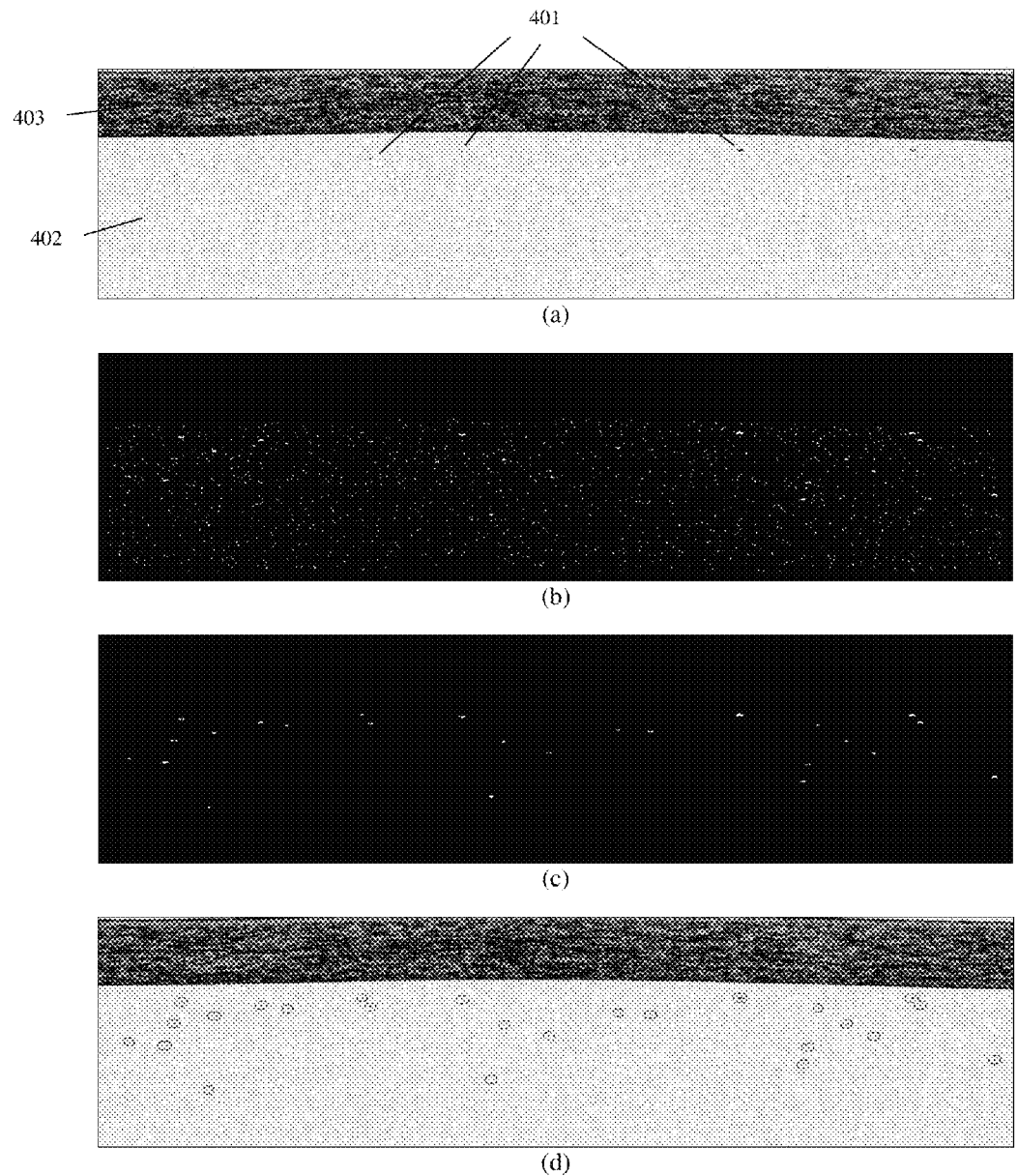
FIG. 4(a) shows an inverted gray scale image of clumps against a bright background.
FIG. 4(b) shows the binary mask created as a step in the inventive method.
FIG. 4(c) shows the result of the segmentation after morphological processing and FIG. 4(d) shows a visualization of the segmented clumps.

We can use the observation that the actual clumps of interest are within a particular size or shape range to place geometric constraints on the analysis of the clumps 205. The other information that is used is that the cell clumps appear as elongated blobs along the horizontal axis. Hence we morphologically filter the initial segmentation mask and retain only connected components in the mask that have areas in a particular range and are oriented along the x-axis to produce a final segmentation 206. FIG. 4(*c*) shows the result of this morphological operation to create the final segmentation mask on a particular B-scan.

Once the final segmentation is complete, it will be possible to visualize 208 or quantify 207 the clumps in various ways to extract additional information. FIG. 4(*d*) shows one such visualization in which all detected clumps are circled. Classification of the clumps into categories like cell clumps and pigment clumps can be done by further analysis of the intensity characteristics of the clumps and morphological characteristics. These classifications might add further diagnostic value to the clinician about the condition of the subject being imaged and eliminate the problem of counting pigment clumps as cell clumps in grading uveitis. In addition, density measurements could be obtained for each type of clump separately.

From the number of clumps found from each OCT B-Scan, a density measurement could be made based on the volume being imaged. In particular, the segmentations could be used to derive quantitative measurements such as number of clumps/B-Scan, size of each clump, density of the clumps/unit area, and density of the clumps/unit volume among others.

Figure 5:
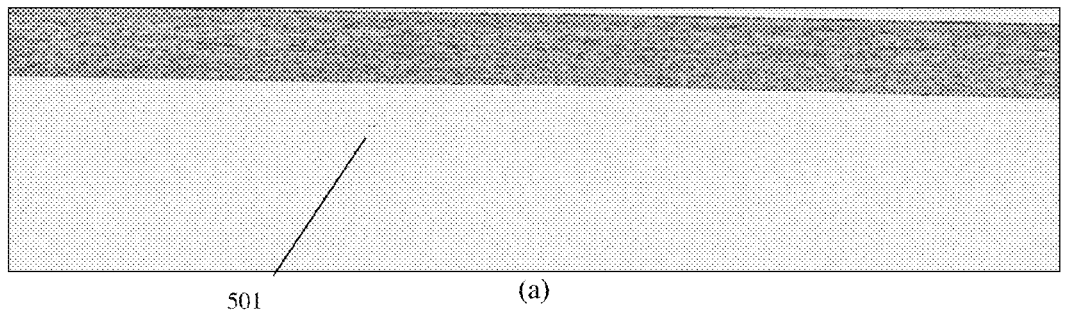
FIG. 5 shows an original image (a) and a visualization of the segmentation (b) from the anterior chamber of a healthy patient.
Figure 5:
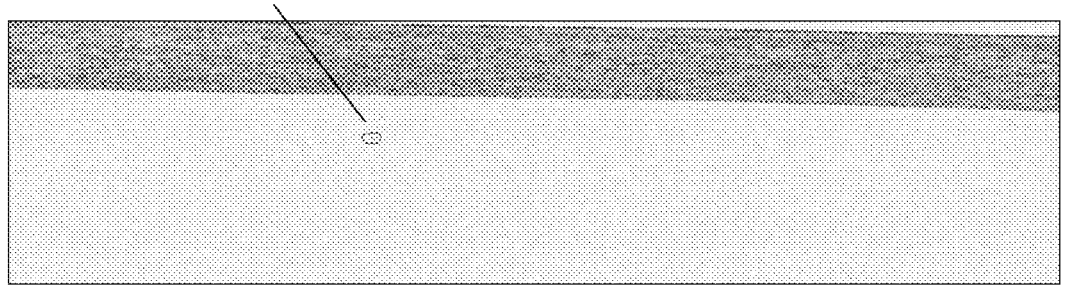
Figure 6:
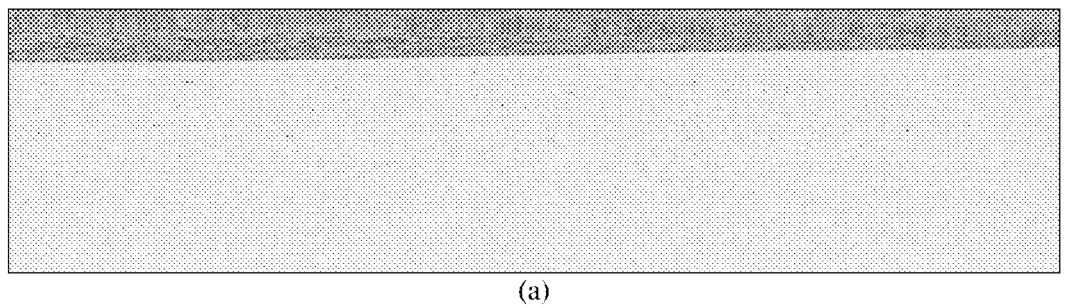
FIG. 6 shows an original image (a) and a visualization of the segmentation (b) from the anterior chamber of a patient with uveitis.
Figure 6:
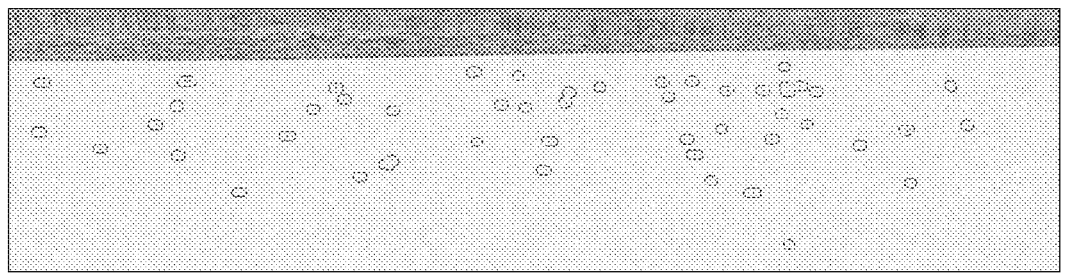

FIGS. 5 and 6 show sample results from representative B-Scans for two different subjects. FIG. 5(*a*) shows the original OCT image of the anterior chamber of a patient while FIG. 5(*b*) shows the segmented image highlighting the cell clump 501 evident in the image. FIG. 6(*a*) and (*b*) show the same types of images for a patient who has undergone surgery for uveitis and as can be seen the density of cell clumps is much larger in that subject indicating inflammatory reaction.

A further aspect of this invention is proposing an easy way to automatically validate or invalidate the generated results based on input from the clinician. A particular embodiment of this would be to display the detected clumps to a user as shown in FIGS. 5(*b*) and 6(*b*) and the user only has to click on or otherwise designate what they believe are false detections, and the system would remove that clump from further calculations. This could be done in the opposite way, where the clinician clicks on the detected clumps they believe are correct, but this would be more time-consuming as it is imagined that the false detections would be fewer than the correct detections. In addition, the various qualitative and quantitative characterizations of cell clumps can be used to grade the disease, track the disease progression over time, and monitor treatment efficacy. Data from two separate examinations at different times can be compared to determine the rate of disease progression and make predictions on future progression.

Although various embodiments that incorporate the teachings of the present invention have been shown and described in detail herein, those skilled in the art can readily devise many other varied embodiments that still incorporate these teachings.

The following references are hereby incorporated by reference:

US Patent Publication No. 2009/0244485 Walsh et al. "Optical Coherence Tomography Device, Method, and System"

Agarwal et al, "High-Speed Optical Coherence Tomography for Imaging Anterior Chamber Inflammatory Reaction in Uveitis: Clinical Correlation and Grading" American Journal of Ophthalmology 147(3): 413-416 2009.

Agarwal et al "Using OCT to assess anterior chamber inflammation" Ophthalmology Times Europe 4(2) March 2008.

Lowder et al. "Anterior Chamber Cell Grading with High-Speed Optical Coherence Tomography" IOVS 2004; 45 E-abstract 3372.

Wojtkowski, et al., "Three-dimensional retinal imaging with high-speed ultrahigh—resolution optical coherence tomography," *Ophthalmology* 112(10):1734 2005.

Lee et al. "In vivo optical frequency domain imaging of human retina and choroid," *Optics Express* 14(10):4403 2006.

Leitgeb et al, "Ultrahigh resolution Fourier domain optical coherence tomography," *Optics Express* 12(10):2156 2004.

Kim et al. "The role of imaging in the diagnosis and management of uveitis" Expert Rev. Ophthalmol. 5(5) 699-713 2010.

What is claimed is:

1. A method for automatically identifying inflammatory clumps within the eye from image data obtained with an optical coherence tomography (OCT) system, the method comprising:

identifying the region of the tissue from within the image data that will be searched for clumps;

identifying locations in the region that have a brightness above a predetermined threshold and have geometric properties that fall within a predetermined range associated with clumps; and displaying or quantifying the identified clumps.

2. A method as recited in claim 1, wherein the step of identifying the region of the tissue from within the image data that will be searched for clumps, includes segmenting the image data.

3. A method as recited in claim 1, wherein prior to identifying the region of the tissue from within the image data that will be searched for clumps, the image data is smoothed.

4. A method as recited in claim 1, wherein an image is generated and displayed that permits visualization of the size and location of the identified clumps.

5. A method as recited in claim 4, wherein the image is displayed in inverted grayscale to enhance visualization.

6. A method as recited in claim 4, wherein the image is displayed to a clinician on a user interface and further comprising validating the automatically detected clumps based on input from the clinician.

7. A method as recited in claim 6, wherein the clinician provides input on false detections.

8. A method as recited in claim 1, wherein the number of identified clumps is calculated and then displayed or stored.

9. A method as recited in claim 8, wherein the number of clumps is used to automatically determine a uveitis grade based on Standardization of Uveitis Nomenclature.

10. A method as recited in claim 1, wherein the density of clumps in the region is calculated and then displayed or stored.

11. A method as recited in claim 1, further comprising analyzing one or both of the intensity characteristics of the clumps and morphological characteristics to categorize the clumps as cell clumps or pigment clumps.

12. A method as recited in claim 11, further comprising separately quantifying properties of each type of clump.

13. A method as recited in claim 1, wherein the volume of the clumps is quantified.

14. A method as recited in claim 1, further comprising classifying the subject into disease categories based on the quantitative information.

15. A method as recited in claim 1, further comprising 3D volume rendering of the clumps.

16. A method as recited in claim 1, further comprising making an assessment on the infection status of the eye of the patient based on the detected clumps.

17. A method as recited in claim 1, further comprising comparing the display or quantitative information on the clumps to measurements from a prior examination and providing the user with change analysis of the measurements to evaluate progression.

18. A method as recited in claim 1, further comprising comparing quantitative information on the clumps to clump data from a prior examination and providing the user with rates of change of particular parameters to evaluate progression.

19. An optical coherence tomography (OCT) system for identifying inflammatory clumps within the eye of a patient, said OCT system comprising:
    a light source arranged to generate a beam of radiation
    a beam divider for separating the beam along a sample arm and a reference arm;
    optics for scanning the beam in the sample arm over a set of transverse locations on the eye;
    a detector for measuring radiation returning from both the sample arm and the reference arm, the detector generating output signals in response thereto; and
    a processor for converting the output signals into image data, said processor identifying the region of the tissue from within the image data that will be searched for clumps and then identifying locations in the region that have a brightness above a predetermined threshold and have geometric properties that fall within a predetermined range associated with clumps.

20. An OCT system as recited in claim 19, further including a display for displaying an image of the eye including the size and location of the identified clumps.

21. An OCT system as recited in claim 20, wherein the image is displayed in inverted grayscale to enhance visualization.

22. An OCT system as recited in claim 20, wherein the image is displayed to a clinician on a user interface that permits the clinician to enter information to validate the identified clumps.

23. An OCT system as recited in claim 20, wherein the processor determines the number of identified clumps and the determined number is displayed on the display.

24. An OCT system as recited in claim 20, wherein the processor quantifies the volume of the clumps and the volume is displayed on the display.

25. An OCT system as recited in claim 19, wherein the processor analyzes one or both of the intensity characteristics of the clumps and morphological characteristics to categorize the clumps as cell clumps or pigment clumps.

26. An OCT system as recited in claim 25, wherein the processor separately quantifies the properties of each type of clump.

27. An OCT system as recited in claim 19, wherein the processor compares the identified clumps to clumps identified in a previous examination of the patient.

* * * * *

UNITED STATES PATENT AND TRADEMARK OFFICE
CERTIFICATE OF CORRECTION

PATENT NO.         : 8,632,180 B2                                    Page 1 of 1
APPLICATION NO.    : 13/449227
DATED              : January 21, 2014
INVENTOR(S)        : Harihar Narasimha-Iyer It is certified that error appears in the above-identified patent and that said Letters Patent is hereby corrected as shown below:

In the Specification

In column 3, line 15, delete "2006)" and insert -- 2006). --, therefor.

In column 5, line 61, delete "System"" and insert -- System". --, therefor.

Signed and Sealed this
Twenty-ninth Day of April, 2014

Michelle K. Lee
*Deputy Director of the United States Patent and Trademark Office*